United States Patent [19]

Watanabe et al.

[11] 4,421,855

[45] Dec. 20, 1983

[54] PRODUCTION OF ACRYLAMIDE USING IMMOBILIZED CELLS

[75] Inventors: Ichiro Watanabe; Keiichi Sakashita, both of Yokohama; Yasuo Ogawa, Kawasaki, all of Japan

[73] Assignee: Nitto Chemical Industry Co., Ltd., Tokyo, Japan

[21] Appl. No.: 292,848

[22] Filed: Aug. 14, 1981

[30] Foreign Application Priority Data

Aug. 19, 1980 [JP] Japan ................................ 55-113039

[51] Int. Cl.³ ...................... C12P 13/02; C12N 11/08; C12N 11/04
[52] U.S. Cl. .................................... 435/129; 435/180; 435/182
[58] Field of Search ............... 435/129, 174, 177, 180, 435/182

[56] References Cited

U.S. PATENT DOCUMENTS

| | | | |
|---|---|---|---|
| 3,859,169 | 1/1975 | O'Driscoll et al. | 435/182 |
| 3,860,490 | 1/1975 | Guttag | 435/182 |
| 4,248,968 | 2/1981 | Watanabe et al. | 435/129 |

*Primary Examiner*—David M. Naff
*Attorney, Agent, or Firm*—Sughrue, Mion, Zinn, Macpeak & Seas

[57] ABSTRACT

A process is described for producing acrylamide from acrylonitrile using an immobilized microorganism containing gel, which comprises immobilizing a microorganism having nitrilasic activity with a cationic acrylamide-based polymer gel and bringing acrylonitrile into contact with the immobilized microorganism gel in an aqueous medium containing substantially no salt.

9 Claims, No Drawings

PRODUCTION OF ACRYLAMIDE USING IMMOBILIZED CELLS

FIELD OF THE INVENTION

The present invention relates to a process for the production of acrylamide using immobilized cells which are prepared by immobilizing microorganisms having nitrilasic activity with a cationic acrylamide-based polymer gel.

BACKGROUND OF THE INVENTION

Acrylamide is in widespread use, for example, as a starting material for the production of various polymers for use as flocculants, stock additives, polymers of petroleum recovery, and so forth.

As a process for the production of such acrylamide, a method has heretofore been known which comprises reacting acrylonitrile with water by the use of a catalyst comprising copper in a reduced state. This method, however, suffers from various problems, for example, with respect to complexity in the preparation of the catalyst, difficulty in regeneration of the used catalyst, and complexity in the separation and purification of acrylamide formed. Furthermore, it is desirable to produce acrylamide under moderate reaction conditions, because compounds containing double bonds in the molecule, such as acryalmide, are readily polymerizable.

It has therefore been considered very desirable to establish a process for producing acrylamide by hydrolyzing acrylonitrile with microorganisms under moderate conditions.

It has long been known that microorganisms having nitrilasic activity are effective in hydrolyzing acrylonitrile to yield acrylamide. As such microorganisms, those belonging to the genera Bacillus, Bacteridium in the sense of Prevot, Micrococcus and Brevibacterium in the sense of Bergey, etc., are known (e.g., see, for example, U.S. Pat. No. 4,001,081). It has also been found that microorganisms belonging to the genera Corynebacterium and Nocardia are useful for the hydrolysis of acrylonitrile (e.g., see U.S. Pat. No. 4,248,968).

In producing acrylamide from acrylonitrile by the use of such microorganisms, acrylonitrile is brought into contact with the microorganisms or immobilized cells thereof prepared by immobilizing the cells with polymer gels, in an aqueous medium such as water, a physiological saline solution, and a phosphate buffer solution. Recently, a batchwise or continuous column method using granulated immobilized cells has been in widespread use, for the purposes of the prevention of elution of impurities from the cells, for improving separation of the cells from a reaction solution, for repeated utilization of the cells, and for increasing the stability of enzymes. Such methods using granulated immobilized cells are advantageous from an economic viewpoint. Therefore, a process has been proposed for the production of acrylamide by a continuous column reaction using immobilized microorganism cells which are prepared by entrapping the cells with a gel of polyacrylamide or the like (e.g., see U.S. Pat. No. 4,248,968).

In the processes as proposed above, however, the use of a physiological saline solution, phosphate buffer solution, or the like as an aqueous medium results in the introduction of large amounts of sodium chloride, phosphates and the like into the aqueous acrylamide solution formed, which is not desirable from the viewpoint of the quality of the desired product. In particular, in the production of acrylamide-based polymers having a high molecular weight, the presence of phosphates in acrylamide is liable to cause water-insolubilization of the polymers formed. For the removal of such salts, therefore, it is essential to apply post-treatments such as an ion exchange treatment. This leads to the loss of the advantage that a high quality acrylamide aqueous solution can be prepared without any special purification step, which is a feature of the method of producing acrylamide by an immobilized cell method. Thus, the advantage of the immobilized cell method as an inexpensive method for the production of acrylamide is lost.

On the other hand, if the physiological saline solution, phosphate buffer solution, or the like is not used as the aqueous medium, the immobilized cells swell in the course of the hydration reaction, and the enzymatic activity of the cells is rapidly lost. Furthermore, in the case of the column reaction, when an aqueous solution of acrylonitrile is passed through a column which is packed with cells conventionally immobilized with polyacrylamide, the immobilized cells in the column swell in a short time after the start of the hydration reaction, as a result of which efficient operation of the method becomes impossible.

Although the reason why the immobilized cells swell during the hydration reaction is not completely clear, it is believed to be due to the repulsion force generated among negatively charged cells in passing a substrate solution thereover, and the difference in osmotic pressure between the outside and inside of the immobilized cells, resulting from the difference in concentrations of acrylonitrile and acrylamide between the outside and inside of the immobilized cells, which occurs when acrylonitrile enters into the immobilized cells and is converted (hydrated) into acrylamide, and the thus-formed acrylamide migrates out of the immobilized cells. Furthermore, it is also believed that the deterioration of the enzymatic activity by the swelling phenomenon is due to the facts that the enzyme is liable to leak out of the immobilized cells due to swelling, and that the stable conformation in normal cells in which the enzyme is not swollen cannot be maintained. Therefore, it is believed that when the reaction is carried out in an isotonic medium such as a physiological saline solution, a phosphate buffer solution, etc., no great difference in osmotic pressure between the outside and inside of the immobilized cells is created, and therefore the swelling of the immobilized cells can be prevented while at the same time the enzyme can be maintained in a stable condition.

SUMMARY OF THE INVENTION

As a result of extensive investigations to prepare immobilized cells which do not swell in the course of the hydration reaction, even though an aqueous substrate solution not containing a salt as described above is employed as the aqueous medium, and which have excellent enzymatic stability, it has been found that such immobilized cells can be prepared by employing an immobilizing polymeric carrier which is enhanced in its affinity for cells or enzyme by rendering it cationic.

The present invention, therefore, provides a process for the production of acrylamide from acrylonitrile using immobilized microorganism cells, wherein the immobilized cells are prepared by immobilizing a microorganism having nitrilasic activity with a cationic acrylamide-based polymer gel and the acrylonitrile is brought into contact with the immobilized cells in an aqueous medium containing substantially no salt.

DETAILED DESCRIPTION OF THE INVENTION

Any microorganisms capable of hydrolyzing acrylonitrile to yield acrylamide can be used in the invention irrespective of the taxonomical classification. For example, Strain N-771 belonging to the genus Corynebacterium, as described in U.S. Pat. No. 4,248,968 and deposited in the Fermentation Research Institute, the Agency of Industrial Science and Technology, Japan under FERM accession number 4445, Strain N-774 belonging to the genus Corynebacterium and deposited under FERM accession number 4446, and N-775 belonging to Nocardia and deposited under FERM accession number 4447 are preferably used. Further, microorganisms as described in U.S. Pat. No. 4,001,081 also are preferably used in the invention.

In the preparation of immobilized cells using such microorganisms, the microorganism may be used in any of the forms of a cell-containing culture medium (cultured medium), washed cell (resting cells) disrupted cells, and the like.

The cationic acrylamide-based polymer as used herein for the immobilization is a copolymer of acrylamide, an cationic ethylenically unsaturated monomer copolymerizable with acrylamide, and a water-soluble cross-linking monomer.

Examples of cationic ethylenically unsaturated monomers copolymerizable with acrylamide include dialkylaminoalkyl acrylate, dialkylaminoalkyl methacrylate, dialkylaminoalkyl acrylamide, dialkylaminoalkyl methacrylamide, and quaternary salts thereof, e.g., dimethylaminoethyl methacrylate, diethylaminoethyl methacrylate, dimethylaminopropyl methacrylamide, diethylaminopropyl methacrylamide, and quaternary salts thereof with dimethyl sulfate, methyl chloride, and the like. These monomers can be used alone or in combination with each other.

Examples of water-soluble cross-linking monomers include methylenebisacrylamide, 1,3-diacrylamidomethyl-2-imidazolidone, diacrylamidomethylethylene urea, diacrylamido methyl ether, ethylene glycol diacrylate, ethylene glycol dimethacrylate, and hexahydro-1,3,5-triacyl-S-triazine.

With regard to the amounts of the three monomers used, the amount of acrylamide is from 50 to 95% by weight, the amount of the cationic ethylenically unsaturated monomer is from 1 to 50% by weight, and the amount of the water-soluble cross-linking monomer is from 0.1 to 20% by weight, based on the total weight of the three monomers.

The immobilized cells for use in the process of the invention are prepared, for example, by a method in which a suspension of microorganism cells and three monomers as described above are mixed and polymerized in the presence of a polymerization catalyst conventionally used in the conventional methods, such as potassium persulfate and dimethylaminopropionitrile, under the conditions of a pH of from 5 to 10, and preferably from 6 to 8, a temperature of 0° C. to 30° C., and preferably 0° C., to 15° C., and a period of from 30 to 60 minutes, to provide a gel in which the cells are immobilized and entrapped.

The amount of the microorganism cells contained in the gel as obtained above is usually from 0.1 to 50% by weight, and preferably from 1 to 20% by weight, based on the total weight of the aqueous gel, although it may vary depending on the type of the microorganism, the state of use thereof, and so forth. The monomer content of the reaction solution is from 2 to 30% by weight, and preferably from 5 to 20% by weight, based on the total weight of solution.

For the preparation of the immobilized cell-containing gel, in addition to the foregoing method in which a cationic portion is added as a monomer and copolymerization is then effected to provide the gel, another method can be employed in which the whole or part of the cationic monomer is previously polymerized to provide a water-soluble polymer which is still capable of being gelled, and the water-soluble polymer is then mixed with the suspension of microorganism cells containing monomers and is reacted to provide the desired gel. Alternatively, the water-soluble polymer to be added before the preparation of the gel may be prepared by copolymerizing the cationic monomer with a part of the acrylamide.

The thus-prepared immobilized cells are shaped into a particular form, if desired, after being subjected to a water-soluble dialdehyde treatment such as glutaraldehyde.

In the practice of the invention, cationically immobilized cells as described above can be pulverized into particles of a suitable size and charged to a reactor or column. By bringing an aqueous solution of acrylonitrile having a salt concentration of 0.1 wt.% or less, and preferably 0.01 wt.% or less, i.e., an aqueous solution of acrylonitrile containing substantially no salt, into contact with the immobilized cells, the desired acrylamide can be prepared. By suitably selecting the amount of the immobilized cells for use in the reaction, the concentration of acrylonitrile, the flow rate of the aqueous substrate solution, and so forth, a conversion of nearly 100% can be attained. In this case, to maintain the nitrilasic activity of the immobilized cells for a long period of time and to inhibit the formation of by-products such as acrylic acid, it is preferred that the concentration of acrylonitrile be 5 wt.% or less, that the reaction temperature be as low as possible within a range such that the aqueous substrate solution does not freeze, i.e., from, just above the freezing point to about 10° C., and that the pH be 7.0 to 8.5.

In accordance with the process of the invention, the reaction can be continued without causing the swelling of the immobilized cells in the course of the reaction, even without the use of a physiological saline solution, a phosphate buffer, or the like as an aqueous substrate solution, and, furthermore, while maintaining the enzyme activity in a stable condition for a long period of time. In particular, in the case of a continuous column reaction, the process of the invention offers, in addition to the foregoing advantage, the advantage that the polymerization of the acrylamide formed (having a tendency to occur in a reactor in the course of the reaction) can be avoided completely and the operation can be stabilized.

Thus, a colorless, transparent aqueous solution of acrylamide can be obtained as a reaction effluent. Since the aqueous solution of acrylamide contains substantially no salt and almost no impurities exerting adverse influences on the polymerization of acrylamide, it can b used, as is or after being concentrated, as a starting material for the production of acrylamide polymers for use as flucculants, stock additives, and so forth.

The following examples and comparative examples are given to illustrate the invention in greater detail. All parts and percents are by weight. The acrylonitrile, acrylamide, and acrylic acid concentrations were measured by gas chromatography.

EXAMPLE 1 and COMPARATIVE EXAMPLE 1

Fifty parts of washed cells (dry cell content, 20%) of Strain N-774 aerobically cultured on a culture medium (pH 7.2) containing 1% glucose, 0.5% peptone, 0.3% yeast extract and 0.3% malt extract was mixed with 4.2 parts of acrylamide, 0.4 part of a methyl chloride quaternary salt of dimethylaminoethyl methacrylate, 0.4 part of methylenebisacrylamide, and 30 parts of a 0.05 M phosphate buffer (pH 7.5, all the phosphates buffers as described hereinafter have the same pH value) to provide a uniform suspension. To the thus-prepared suspension were added 5 parts of a 5% aqueous solution of dimethylaminopropionitrile and 10 parts of a 2.5% aqueous solution of potassium persulfate, and polymerization was carried out while maintaining a temperature of 10° C. or less for 1 hour to provide a cell-containing gel. The thus-prepared bulky cell-containing gel was pulverized into fine paticles by the use of a blender (Model VA-10P, produced by Hitachi Ltd.), was mixed with 300 parts of a 0.05 M phosphate buffer and 0.5 part of a 50% aqueous solution of glutaraldehyde, and was subjected to a glutataldehyde treatment at 10° C. or less for 30 minutes while stirring. Thus-prepared immobilized cells were washed with water and employed as a sample for the preparation of acrylamide from acrylonitrile as described hereinafter.

Ten parts of the sample and 90 parts of water were mixed. To the resulting mixture, acrylonitrile was dropwise added intermittently at a rate of 2 parts per hour while maintaining the pH at 7.5 with stirring, and the reaction to form acrylamide was conducted at 10° C. for 6 hours. The reaction proceeded almost quantitatively, and 110 parts of a 14.6% aqueous solution of acrylamide was obtained. After repeating the reaction, the residual activity of the immobilized cells was determined.

For comparison, immobilized cells were prepared using conventional polyacrylamide, i.e., the comparative immobilized cells were prepared in the same manner as described above, except that 4.6 parts of acrylamide and 0.4 part of methylenebisacrylamide were used to prepare the immobilized cells. The thus-prepared immobilized cells were used to effect the same reaction to form acrylamide as described above. After the reaction was completed, the residual activity of the immobilized cells were determined.

The results are shown in Table 1.

The residual activity of the immobilized cells was determined as follows:

The immobilized cell sample was fully ground in a mortar and was diluted with a 0.1 M phosphate buffer to prepare a suspension having a cell content of 0.1%. To 5 ml of the suspension was added 5 ml of a 5% aqueous solution of acrylonitrile, and the acrylonitrile was hydrolyzed at 10° C. For 10 minutes to yield acrylamide. The amount of the acrylamide formed was measured. The residual activity of the immobilized cells was expressed by the ratio of the amount of the acrylamide present after the reaction to the amount of the acrylamide present before the reaction.

TABLE 1

| Number of Repetitions of Reaction | Residual Ratio of Activity (%) | |
|---|---|---|
| | Example 1 | Comparative Example 1 |
| 0 | 100 | 100 |
| 1 | 95 | 80 |
| 3 | 90 | 55 |
| 5 | 85 | 30 |
| 7 | 80 | 0 to 5 |

EXAMPLE 2 and COMPARATIVE EXAMPLE 2

Forty parts of immobilized cells as prepared in EXAMPLE 1, i.e., Strain N-774 immobilized with acrylamidedimethylaminoethyl methacrylate methyl chloride quaternary salt copolymer gel, was charged into a jacketed glass column. A 4% aqueous solution of acrylonitrile (adjusted to pH 7.5 with sodium carbonate) was introduced into the glass column from the top thereof and passed therethrough at a temperature of 5° C. and at a space velocity (SV) of 0.8 hr$^{-1}$ to effect the reaction.

During the reaction, no swelling of the immobilized cell particles in the glass column was observed, and the apparent packing volume did not change, (i.e., volume remained almost constant. Thus the operation could be stably continued for a long period of time.

A colorless transparent aqueous solution of acrylamide was obtained as an effluent from the bottom of the glass column, i.e., a bottom effluent. Analysis of the bottom effluent obtained 5 days after the start of the reaction showed that it contained 5.4% of acrylamide, and acrylonitrile was not detected at all.

For comparison, the same comparative immobilized cells as prepared in EXAMPLE 1 was used to effect the same column reaction as described above. Shortly after the start of the reaction, the immobilized cells began to swell, and the operation could not be performed smoothly. Five days after the start of the reaction, the activity of the swollen immobilized cells was determined and found to be about 1/10 of the original activity.

EXAMPLES 3 to 8 and COMPARATIVE EXAMPLE 3

Washed cells of Strain N-774 as prepared in EXAMPLE 1 were immobilized in the same manner as in EXAMPLE 1 except that instead of the acrylamide, dimethylaminoethyl methacrylate and methylenebisacrylamide were used as monomers for the polymerization, the proportions of acrylamide and dimethylaminoethyl methacrylate were changed as indicated below, and the polymerization was performed in an atmosphere of nitrogen.

Using the thus-prepared immobilized cells, the reaction of forming acrylamide from acrylonitrile was conducted by the same batchwise method and under the same conditions as used in EXAMPLE 1. The reaction was repeated, and the residual activity was determined.

The results are shown in Table 2. As can be seen from Table 2, the copolymerization of dimethylaminoethyl methacrylate increases enzyme stability.

TABLE 2

| | Example | | | | | | Comparative Example |
|---|---|---|---|---|---|---|---|
| | 3 | 4 | 5 | 6 | 7 | 8 | 3 |
| Polymer composition for Immobilized Cells (%) | | | | | | | |
| Acrylamide | 94 | 90 | 85 | 80 | 70 | 50 | 95 |
| Dimethylaminoethyl Methacrylate | 1 | 5 | 10 | 15 | 25 | 45 | 0 |
| Methylenebisacrylamide | 5 | 5 | 5 | 5 | 5 | 5 | 5 |
| Residual Ratio of Activity (%) | | | | | | | |
| Number of Repetitions of Reaction: 0 | 100 | 100 | 100 | 100 | 100 | 100 | 100 |
| Number of Repetitions of Reaction: 1 | 90 | 95 | 95 | 95 | 95 | 80 | 80 |
| Number of Repetitions of Reaction: 3 | 85 | 85 | 85 | 85 | 80 | 65 | 55 |
| Number of Repetitions of Reaction: 5 | 80 | 80 | 80 | 80 | 75 | 60 | 30 |

EXAMPLES 9 to 14

Using washed cells of Strain N-774 as prepared in EXAMPLE 1, immobilized cells having the polymer compositions shown in Table 3 were prepared. In EXAMPLES 11 to 14, the polymerization was performed in the presence of cationic water-soluble polymers as indicated below which has been prepared in advance to thereby prepare immobilized cells. Using the thus-prepared immobilized cells, the batchwise reaction of forming acrylamide from acrylonitrile was repeated in the same manner as in EXAMPLE 1. After the reaction was completed, the residual activity of each immobilized cell gel was determined.

The results are shown in Table 3. It can be seen from Table 3 that the immobilized cells prepared in accordance with the process of the invention hold stable enzyme activity for long periods of time even in substrate solutions containing substantially no salts.

TABLE 3

| | Example | | | | | | Comparative Example |
|---|---|---|---|---|---|---|---|
| | 9 | 10 | 11 | 12 | 13 | 14 | 3 |
| Polymer Composition in Immobilized Cells (%) | | | | | | | |
| Acrylamide | 87 | 82 | 75 | 75 | 75 | 75 | 95 |
| Methyl chloride quaternary salt of dimethylethyl methacrylate | 5 | — | — | — | — | — | — |
| Dimethylaminopropylmethacrylamide | — | 10 | — | — | — | — | — |
| Methylenebisacrylamide | — | — | 5 | 5 | 5 | 5 | 5 |
| 1,3-Di-acrylamidomethyl-2-imidazolidone | 8 | 8 | — | — | — | — | — |
| Polymer of methyl chloride quaternary salt of dimethylaminoethyl methacrylate (Mw., about 500,000) | — | — | 20 | — | — | — | — |
| Polymer of dimethylaminoethyl methacrylate (Mw., about 1,000,000) | — | — | — | 20 | — | — | — |
| Copolymer of acrylamide and methyl chloride quaternary salt of dimethylaminoethyl methacrylate (Mw., about 500,000) | — | — | — | — | 20 | — | — |
| Copolymer of acrylamide and dimethylaminoethyl methacrylate (Mw., about 2,000,000) | — | — | — | — | — | 20 | — |
| Residual Ratio of Activity (%) | | | | | | | |
| Number of repeated reactions 0 | 100 | 100 | 100 | 100 | 100 | 100 | 100 |
| Number of repeated reactions 1 | 95 | 95 | 95 | 90 | 95 | 90 | 80 |
| Number of repeated reactions 3 | 90 | 85 | 85 | 85 | 90 | 85 | 55 |
| Number of repeated reactions 5 | 80 | 85 | 85 | 80 | 85 | 85 | 30 |

While the invention has been described in detail and with reference to specific embodiments thereof, it will be apparent to one skilled in the art that various changes and modifications can be made therein without departing from the spirit and scope thereof.

What is claimed is:

1. A process for producing acrylamide from acrylonitrile in an aqueous medium by the action of a microorganism having nitrilasic activity immobilized with a polyacrylamide gel wherein the improvements comprise immobilizing the microorganism by the use of cationic acrylamide-based polymer gel comprising from 50 to 95% by weight acrylamide, from 1 to 50% by weight of at least one cationic ethylenically unsaturated monomer copolymerizable with acrylamide selected from the group consisting of dimethylaminoethyl methacrylate, diethylaminoethyl methacrylate, dimethyolaminopropylmethacrylamide, diethylaminopropylmethacrylamide, and quaternary salts thereof, and from 0.1 to 20% by weight of a cross-linking monomer, based on the total weight of the three monomers and using as said medium, an aqueous medium having a salt concentration of 0.1 weight percent or less.

2. A process as in claim 1, wherein immobilizing the microorganism cells by use of said cationic acrylamide-based polymer gel is carried out by polymerizing a mixture of the acrylamide, the cationic ethylenically unsaturated monomer, and the water-soluble cross-linking monomer in an aqueous suspension of the microorganism having nitrilasic activity.

3. A process as in claim 1, wherein immobilizing the microorganism cells by use of said cationic acrylamide-based polymer gel is carried out by polymerizing a mixture of the acrylamide and the water-soluble cross-linking monomer in an aqueous suspension of the microorgamnism having nitrilasic activity and in the presence of a water-soluble cationic polymer containing the cationic ethylenically unsaturated monomer, or by polymerizing a mixture of the acrylamide, the cationic ethylenically unsaturated monomer, and the water-soluble cross-linking monomer in an aqueous suspension of the microorganism having nitrilasic activity and in the presence of a water-soluble cationic polymer containing the cationic ethylenically unsaturated monomer.

4. A process as in claim 3, wherein the water-soluble cationic polymer is at least one polymer selected from the group consisting of homopolymers of said cationic ethylenically unsaturated monomer and copolymers of said cationic ethylenically unsaturated monomers and acrylamide.

5. A process as in claim 1, 2, or 3, wherein the microorganism content of the immobilized microorganism-containing gel is from 0.1 to 50% by weight.

6. A process as in claim 5, wherein the microorganism content of the immobilized microorganism-containing gel is from 1 to 20% by weight.

7. A process as in claim 2 or 3, wherein the process is carried out at a pH of from 5 to 10 and a temperature of from 0° C. to 30° C.

8. A process as in claim 2 or 3, wherein the process is carried out at a pH of from 6 to 8 and a temperature of from 0° C. to 15° C.

9. A process as in claim 1 wherein the aqueous medium has a salt content of 0.01 weight percent or less.

* * * * *